US00PP09281P

United States Patent [19]

Olesen et al.

[11] Patent Number: Plant 9,281

[45] Date of Patent: Sep. 12, 1995

[54] MINIATURE ROSE PLANT NAMED 'POULTORY'

[75] Inventors: Mogens N. Olesen; Pernille Olesen, both of Fredensborg, Denmark

[73] Assignee: Bear Creek Gardens, Inc., Medford, Oreg.

[21] Appl. No.: 150,454

[22] Filed: Nov. 9, 1993

[51] Int. Cl.[6] ..... H01H 5/00

[52] U.S. Cl. ..... Plt./10

[58] Field of Search ..... Plt. 10, 10.1, 9, 7.1

[56] References Cited

U.S. PATENT DOCUMENTS

P.P. 8,012 10/1992 Olesen et al. ..... Plt./10

*Primary Examiner*—Howard J. Locker

*Attorney, Agent, or Firm*—Klarquist Sparkman Campbell Leigh & Whinston

[57] ABSTRACT

A rose plant of the miniature class, a mutation of the variety POULvic, having a different flower color, new growth color and petal count from its parent.

1 Drawing Sheet

The present invention relates to a new and distinct variety of rose plant of the miniature class which was discovered by us as a spontaneous mutation of the variety POULvic, U.S. Plant Pat. No. 8,012.

POULtory is unique and distinct from its parent variety, POULvic, principally in its flower color. Instead of having petals that are of Red Group 45C, the petals are of Red Group 53B. The parent variety has an average petal count of 60 petals, whereas POULtory has an average petal count of 40 to 50 petals. POULvic has new growth that is somewhat reddish, while POULtory is more of a light lime green. There are other distinctions as well that may be observed from comparison of the features herein described and those set forth in U.S. Plant Pat. No. 8,012 for its parent, POULvic.

Asexual reproduction of this new variety by budding and by softwood cuttings as performed at Fredensborg, Denmark, and Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with the Royal Horticultural Society (London) Colour Chart, except where ordinary dictionary significance of color is indicated.

Classification:

*Botanical.*—*Rosa hybrida.*

*Commercial.*—Miniature.

FLOWER

Observations made from specimens grown in a garden environment at Fredensborg, Denmark, in 1991.

Blooming habit: Continuous.

Bud:

*Size.*—1.3 cm long when the petals start to unfurl.

*Form.*—Short, pointed ovoid.

*Color.*—When sepals first divide, bud color is Red Group 53B. When half blown, the upper sides of the petals are Red-Purple Group 57C, and the lower sides of the petals are Red Group 53B.

*Sepals.*—Color: Green Group 137C. Surface texture: Smooth with a few fine hairs. There are three lightly appendaged sepals having elongated tips. There are two unappendaged sepals with hairy edges.

*Receptacle.*—Color: Green Group 137C. Shape: Funnel. Size: Small (0.3 cm×0.3 cm). Surface: Smooth.

*Peduncle.*—Length: Short (3.8 cm×5.1 cm). Surface: Numerous small glandula present. Color: Medium green. Strength: Stiff, erect, slender.

Bloom:

*Size.*-Small. Average open size is 2.5 cm in diameter.

*Borne.*—Several together, in flat clusters of three to five blooms.

*Stems.*—Short, strong (average length is 15.2 cm).

*Form.*—When first open: High centered. Permanence: Flattens, outer petals curl back.

*Petalage.*—Number of petals under normal conditions: 40 to 50.

*Color.*—The upper side of the petals is Red-Purple Group 57C. The reverse side of the petals is Red Group 53B. The base of each petal has a small (3 mm×4 mm) White Group 155B half moon at the point of attachment. The major color on the upper side is Red Purple Group 57C.

*Variegations.*—None.

*Discoloration.*—The general tonality at the end of the first day: No change. At the end of the third day, there is a gradual change to Red-Purple Group 57D.

*Fragrance.*—Slight.

Petals:

*Texture.*—Thin.

*Shape.*—Round.

*Form.*—Tips slightly recurved; edges are slightly quilled.

*Arrangement.*—Imbricated, with few petaloids in the center.

*Persistence.*—Drop off cleanly.

*Lastingness.*—On the plant: Very long (10 to 14 days). As a cut flower: Very long (10 days).

Reproductive Parts:

*Anthers.*—Size: Small. Quantity: Few. Color: Yellow. Arrangement: Regular around styles.

*Filaments.*—Color: Reddish brown.

*Pollen.*—Color: Lemon yellow.

*Styles.*—Color: Creamy white.

*Stigmas.*—Color: Greenish white.

Form: Bush.

Growth: Dwarf, upright, branching.

Foliage: Number of leaflets on normal mid-stem leaves: 5.

*Size.*—Small (6.4 cm×3.8 cm).

*Quantity.*—Normal.

*Color.*—*New foliage: Green Group* 143B. Old foliage: Green Group 137A.

Leaflets:

*Shape.*—Pointed oval.

*Texture.*—Upper side: Leathery, smooth.

*Edge.*—Serrated.

*Serration.*—Small.

*Petiole rachis.*—Color: Green.

*Petiole underside.*—Smooth with an occasional prickle.

*Stipules.*—Short (1 cm), bearded.

*Disease resistance.*—Resistant to mildew under normal growning conditions in a garden environment in Fredensborg, Denmark.

Wood:

*New wood.*—Color: Light green. Bark: Smooth.

*Old wood.*—Color: Green. Bark: Smooth.

Prickles:

*Quantity.*—Few on main canes from base and on laterals from main canes.

*Form.*—Short (3 and 4 mm), straight.

*Color when young.*—Green.

Small prickles:

*Quantity.*—None on main stalks. Few on laterals.

We claim:

1. A new and distinct variety of rose plant of the miniature class, substantially as herein shown and described, a mutation of the variety POULvic, U.S. Plant Pat. No, 8,012, characterized particularly as to novelty by its difference in flower color, new growth color and petal count from its parent.

* * * * *

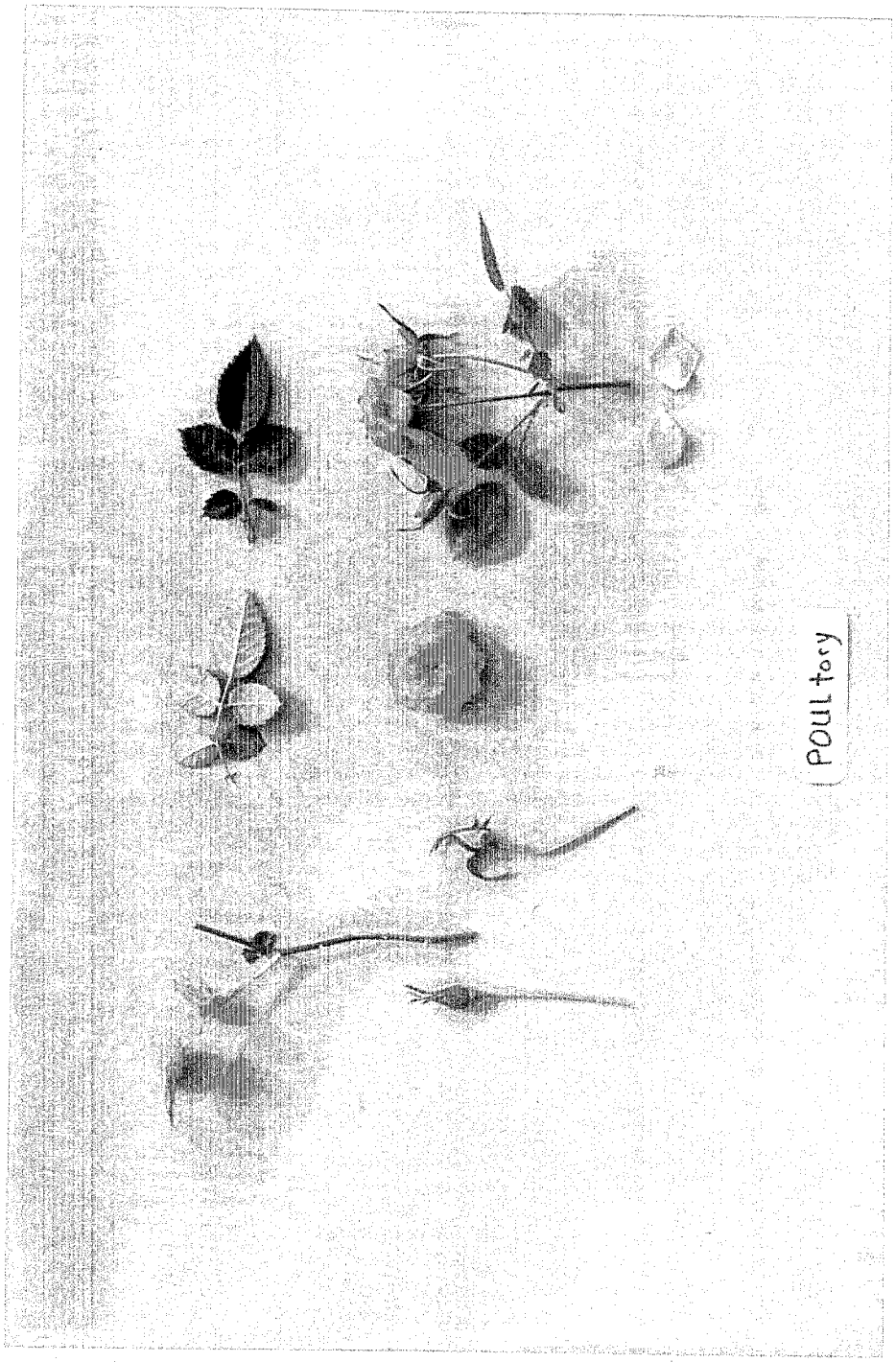
POULtory